United States Patent
Hu et al.

(10) Patent No.: US 10,578,626 B2
(45) Date of Patent: Mar. 3, 2020

(54) KIT FOR RAPIDLY TESTING MYOCARDIAL INFARCTION AND A PREPARATION METHOD AND AN APPLICATION THEREOF

(71) Applicants: Eachy Biopharmaceuticals Co., Ltd., Suzhou, Jiangsu (CN); Wenbo Hu, Beijing (CN)

(72) Inventors: Wenbo Hu, Beijing (CN); Jing Li, Jiangsu (CN)

(73) Assignees: EACHY BIOPHARMACEUTICALS CO., LTD., Suzhou (CN); Wenbo Hu, Beijing (CN)

( * ) Notice: Subject to any disclaimer, the term of this patent is extended or adjusted under 35 U.S.C. 154(b) by 512 days.

(21) Appl. No.: 15/313,034

(22) PCT Filed: Apr. 15, 2015

(86) PCT No.: PCT/CN2015/076625
§ 371 (c)(1),
(2) Date: Jan. 23, 2017

(87) PCT Pub. No.: WO2015/176589
PCT Pub. Date: Nov. 26, 2015

(65) Prior Publication Data
US 2017/0219608 A1 Aug. 3, 2017

(30) Foreign Application Priority Data

May 22, 2014 (CN) .......................... 2014 1 0217355
Jan. 9, 2015 (CN) .......................... 2015 1 0012402

(51) Int. Cl.
*G01N 33/68* (2006.01)
*G01N 33/533* (2006.01)
*G01N 33/543* (2006.01)
*G01N 33/558* (2006.01)

(52) U.S. Cl.
CPC ....... *G01N 33/6893* (2013.01); *G01N 33/533* (2013.01); *G01N 33/54313* (2013.01); *G01N 33/558* (2013.01); *G01N 2333/47* (2013.01); *G01N 2333/4704* (2013.01); *G01N 2333/4712* (2013.01); *G01N 2333/70567* (2013.01); *G01N 2333/908* (2013.01); *G01N 2800/324* (2013.01)

(58) Field of Classification Search
None
See application file for complete search history.

(56) References Cited

U.S. PATENT DOCUMENTS

2005/0130120 A1* 6/2005 Lambotte ......... G01N 33/54366 435/4
2008/0010024 A1* 1/2008 Diamond ........... G01N 33/6887 702/19

FOREIGN PATENT DOCUMENTS

| CN | 101806804 | 8/2010 |
|---|---|---|
| CN | 102520192 | 6/2012 |
| CN | 103033624 | 4/2013 |
| CN | 103217535 | 7/2013 |
| CN | 203101403 | 7/2013 |
| CN | 103954778 | 7/2014 |
| CN | 104569412 | 4/2015 |
| CN | 204330776 | 5/2015 |

OTHER PUBLICATIONS

International search report dated Jul. 9, 2015 from corresponding application No. PCT/CN2015/076625.

* cited by examiner

*Primary Examiner* — Rebecca L Martinez
(74) *Attorney, Agent, or Firm* — Hauptman Ham, LLP

(57) ABSTRACT

Disclosed are a kit for testing myocardial infarction rapidly and a preparation method and use thereof. The kit comprises a strip capable of detecting three markers, namely, human myeloperoxidase (MPO), heart-fatty acid binding protein (FABP3) and cardiac troponin I (cTnI) simultaneously. The strip comprises a sample pad, a conjugate pad, a chromatographic membrane coated with three test lines and a quality control line, and a sample absorption pad. Antibodies of the three markers are all marked on the conjugate pad. The chromatographic membrane has three test lines formed by coating paired antibodies of the three markers respectively, the paired antibodies of the three markers being able to specifically combine with the three markers, respectively. The kit has advantages such as convenient operation, rapid response, high sensitivity and high specificity, point of care test, and economical and practical etc.

9 Claims, No Drawings

KIT FOR RAPIDLY TESTING MYOCARDIAL INFARCTION AND A PREPARATION METHOD AND AN APPLICATION THEREOF

RELATED APPLICATIONS

The present application is a National Phase of International Application Number PCT/CN2015/076625, filed Apr. 15, 2015, and claims the priority of China Application Nos. 2 201410217355.6, filed May 22, 2014 and 201510012402.8, filed Jan. 9, 2015, which are incorporated herein by reference in their entireties.

TECHNICAL FIELD

The present invention relates to a kit for testing myocardial infarction rapidly and a preparation method and use thereof.

BACKGROUND

Acute myocardial infarction (AMI) is a serious threat to human health. It is one of the most main diseases that lead to mortality and disability. Quick diagnosis of early acute myocardial infarction combined with timely treatment is the key to reducing patient mortality. For patients who do not experience typical chest pain or whose electrocardiography do not show obvious changes, it is difficult to be accurately diagnosed by solely relying on EKG, echocardiography and cardiac magnetic resonance. Therefore, detecting serum cardiac markers are necessary criteria for diagnosing of AMI.

The cardiac markers are a series of biochemical substances that can be measured in the blood, and are cardiac-specific, and are released in large quantity into the patients' blood circulation when patients experience myocardial injury, and can diagnose myocardial injury by measuring changes of their concentration levels in the blood, thus can be used as monitoring markers for screening, diagnosing, and evaluating prognosis and treatments for myocardial injury. Various cardiac markers have been consistently discovered in clinical practice that indicate myocardial injury, including indicators for myocardial ischemic injury such as Ischemia Modified Albumin and myeloperoxidase etc., and indicators for myocardial necrosis such as cardiac troponin etc. Cardiac markers provide convenience for clinic that enhances the diagnosis and prognosis for myocardial injury.

AMI happens in a short time and does not possess specific precursor symptoms. It is typically difficult to timely diagnose AMI, especially in early stage. Therefore, only the cardiac markers that increase rapidly during the early stage can be used as a warning sign, so that patients can receive timely medical rescue to avoid myocardial damage. In recent years, clinical studies has shown that Heart-type fatty acid binding protein (H-FABP) and myeloperoxidase (MPO) are closely linked to the diagnosing and predicting AMI risk of the patients with acute coronary syndrome. They are new markers for predicting risk of myocardial damage.

Myeloperoxidase (MPO) is a marker for atherosclerosis lesion instability and stress reaction of neutrophils as well as a risk prediction of AMI. MPO is a type of peroxidase that mainly exists in the azurophilic granule of neutrophils or monocyte. Neutrophils will be activated during inflammation, degranulated and released MPO. This can lead to the coronary artery atherosclerotic lesions instability or even its ruptures, exposing the collagen in intravascular subcutaneous tissue. Consequently, it will form platelet adhesion, aggregation, as well as thrombosis, which in turn causes coronary artery occlusion, acute coronary syndrome, and even serious irreversible myocardial ischemic injury. Therefore, MPO may reflect the same pathogenesis of acute myocardial ischemia such as cardiovascular partial activation of neutrophil activation, infiltration and degranulation and ischemia-reperfusion injury. Numerous clinical studies have shown that patients with acute coronary syndrome have significantly elevated levels of MPO in their blood serum. MPO is a new predictor for major adverse cardiovascular diseases of patients with ACS. MPO levels are a risk predictor of adverse cardiac events before AMI occurred. It had raised in first two hours of myocardial ischemia, in this period troponin remained within reference intervals. It shows the potential benefit of MPO on risk stratification of patients with chest pain. Thus, MPO levels can be used to determine treatment and prognosis of coronary heart disease.

Heart-type fatty acid binding protein (FABP3) is an important intracellular fatty acid binding protein with high cardiac specificity, and is present in large quantity in myocardial tissues. Myocardial cell permeability significantly changes during AMI. During the early stages of cell membrane breakage, FABP3 in the myocardial cells leaks into the extracellular fluid or blood circulation. FABP3 can be found in the blood as early as 1-3 hours after the onset of chest pain, 6-8 hours to reach the peak, and returns to normal level in the blood plasma within 24-30 hours. Studies have shown that the sensitivity and positive predictive value of FABP3 are significantly higher than those of cTnI within 3 hours of chest pain, excluded AMI patients without FABP3 changing. FABP3 can predict the risk of adverse cardiac events, as an early marker of AMI.

Cardiac troponin (cTn) is a structural protein composed of striated muscle. Its main function is to regulate myocyte contraction. CTn is composed of cardiac troponin T (cTnT), cardiac troponin I (cTnI) and troponin C (TnC). It plays an important role in the control of cardiac contractility. Blood levels of CTnI are generally lower than 0.3 μg/L in health. When critical myocardial ischemia occurred, myocardial cell membrane integrity gets destroyed, CTnI easily released into the blood since its small molecular weight, and increased after chest pain occurred 4-6 hours, which sustains for another 6-7 days. Because cardiac troponin only exists in cardiac muscles, it is the first choice for the evaluation of myocardial necrosis markers, and is the gold standard for detecting myocardial injury. Currently, cardiac troponin is mainly used for clinical diagnosis, risk assessment and prognosis of myocardial ischemic injury.

Current technologies for detecting MPO, FABP3, cTnI include ELISA, chemiluminescence, turbidimetric immunoassay and the colloidal gold lateflow immunoassay. Colloidal gold lateflow immunoassay requires less sample and is more easily operated, making it suitable for rapid detection of AMI. However, most colloidal gold lateflow immunoassay kits on the market only have a single indicator. Data obtained is usually simple, incomplete, has low detection sensitivity and specificity, and cannot fully reflect the situation of early myocardial infarction in patients, which makes it prone to misdiagnosis or delayed diagnosis. MPO can indicate risks 3 hours before AMI, but other indicators of inflammation can also lead to elevated MPO. On the other hand, FABP3 levels only change 1-3 hours after myocardial infarction and thus cannot be used as a predictor. CTnI is only detectable 4-6 hours after chest pain.

Currently, conventional triple test kit for clinical detects myoglobin, creatine kinase MB isoenzyme, and troponin.

The capability of the tripe test kit is limited due to several reasons-late diagnosis, low accuracy, sensitivity, and poor specificity in early stage of AMI. Although troponin is the gold standard for the diagnosis of AMI, but only after 4-6 hours AMI troponin can be detected in serum. Due to the time lag, it is not an early marker of myocardial necrosis. This in turn has caused as many as 24% of patients to be misdiagnosed due to normal ECG and troponin assays. Similarly, CK-MB increased 4-8 hours after chest pain, and Myoglobin increased at 2-4 hours after infarction. Troponin and CK-MB elevated 4 hours after myocardial infarction, which makes it unable to provide early warning to AMI. Although Myoglobin is released into the blood two hours earlier than Troponin and CK-MB, it may raise in the condition of kidney or skeletal muscle damage, so it has poor cardiac specificity. As a consequence, triple test kit of AMI resulted in a number of patients to be misdiagnosed due to lack of sensitivity and specificity in early stage of AMI. The conventional kit can only show after myocardial infarction occurred not is a predictor of AMI.

Although ECG may also reflect the patient's condition, more than half of the patients who just start to experience chest pain have normal ECG results, thus resulting in their death due to delayed diagnosis.

Through examining existing products and literature, the detection of MYO, cTnI, CK-MB is characterized by time-lag and low accuracy in early stage of AMI; whereas existing technologies and product form for MPO, FABP3, cTnI detection can only be used as a single indicator and cannot act as a timely warning for developing AMI. Currently, MPO, FABP3 and cTnI are used in clinical practice in different product forms, thus have poor compatibility due to different production and procedures, making it difficult to detect the three indicators quickly.

This invention will bring about the following benefits: improved sensitivity of diagnosing for myocardial infarction, higher accuracy of diagnosing for myocardial infarction, an earlier diagnosis of diagnosing for myocardial infarction and dynamical monitoring the process and prognosis of myocardial infarction.

SUMMARY

Technical problem to be solved by the present invention is to overcome the deficiencies of the prior art, and provide a kit that can provides early warning and risk judgment of myocardial infarction rapidly and accurately.

The present invention also provides a preparation method and use of the kit.

In order to solve the above technical problem, a technical solution of the present invention is as below.

A kit for testing myocardial infarction rapidly, comprising a strip capable of detecting three markers, namely, human myeloperoxidase (MPO), heart-fatty acid binding protein (FABP3) and cardiac troponin I (cTnI) simultaneously.

Furthermore, the strip comprises a sample pad, a conjugate pad, a chromatographic membrane coated with three test line and a quality control line, and a sample absorption pad, detecting antibodies of the three markers being all marked on the conjugate pad, and the chromatographic membrane having three test lines formed by coating paired antibodies of the three markers respectively, the paired antibodies of the three markers being able to specifically combine with the three markers, respectively.

According to a specific aspect of the present invention, the conjugate pad is a colloidal gold pad, and the kit is a colloidal gold immunoassay kit. Or, the conjugate pad is a fluorescence microparticles conjugate pad, and the kit is a fluorescence microparticles immunoassay kit.

Preferably, the kit further comprises a colourimetric card and/or a colloidal gold quantitative reader. Or, the kit further comprises an immunofluorescence quantitative reader.

According to a specific aspect, the kit is a colloidal gold immunoassay kit. The kit comprises a standard colourimetric card, the standard colourimetric card comprises three lines red lines from light to dark red which are printed on a white background, which are standard lines of three markers, the different shades of color of each red line represent the different concentration of each standard sample. Furthermore, the detection thresholds of MPO, H-FABP and cTnI are 3 ng/ml, 3 ng/ml and 0.1 ng/ml, respectively. Furthermore, the detection thresholds of the kit for detecting MPO, H-FABP and cTnI are 6.25 ng/ml, 30125 ng/ml and 0.1 ng/ml, respectively. Preferably, there are seven red lines having different shades that correspond to MPO, and correspond to concentrations of 400, 200, 100, 50, 25, 12.5, 6.25 ng/ml. There are seven red lines having different shades that correspond to H-FABP, and correspond to concentrations of 200, 100, 50, 25, 12.5, 6.25, 3.125 ng/ml. There are six red lines having different shades that correspond to cTnI, and correspond to concentrations of 20.0, 10.0, 5.0, 2.0, 0.5, 0.1 ng/ml.

Furthermore, the conjugate pad is a gold colloidal gold pad, the three markers' detective antibody are anti-human myeloperoxidase mouse monoclonal antibody, anti-heart-fatty acid binding protein mouse monoclonal antibody and anti-cardiac troponin I mouse monoclonal antibody, paired antibodies of the three markers are anti-human myeloperoxidase monoclonal or polyclonal antibody, anti-heart-fatty acid binding protein monoclonal or polyclonal antibody, anti-cardiac troponin I monoclonal or polyclonal antibody, respectively.

Preferably, the strip comprises a sample pad, a conjugate pad, a chromatographic membrane and absorbent pad which are stickered on a base pad successively, the three test lines of the chromatographic membrane are parallel and are sequentially arranged along the length of the chromatographic membrane, the test line close to the conjugate pad coats paired antibody of human myeloperoxidase, the test line close to the absorbent pad coats paired antibody of cardiac troponin I, the test line in the middle coats paired antibody of heart-fatty acid binding protein.

According to another specific aspect of the present invention, the conjugate pad is a fluorescence microparticles conjugate, the three markers' detective antibody are anti-human myeloperoxidase mouse monoclonal antibody, anti-heart-fatty acid binding protein mouse monoclonal antibody and anti-cardiac troponin I mouse monoclonal antibody, paired antibodies of the three markers are anti-human myeloperoxidase monoclonal or polyclonal antibody, anti-heart-fatty acid binding protein monoclonal or polyclonal antibody, anti-cardiac troponin I monoclonal or polyclonal antibody, respectively.

Preferably, according to a further specific and preferred aspect of the present invention, the conjugate pad is a fluorescence microparticles conjugate pad, and the kit is a fluorescence microparticles immunoassay kit, wherein the kit further comprises an immunofluorescence quantitative reader.

Preferably, preparation method of the fluorescence microparticles conjugate pad comprising: first, mixing the fluorescence microparticles with the three markers antibodies to obtain the antibody labeled fluorescence microparticles, then spreading the antibody labeled fluorescence microparticles on a glass fiber membrane or non-woven fabrics to obtain the fluorescence microparticles conjugate pad.

Preferably, the fluorescent substance is excited fluorescent substance.

Another technical solution of the present invention is as below.

A preparation method of the kit for testing myocardial infarction rapidly comprising following steps:
(1) preparing the colloidal gold pad, which comprises preparing colloidal gold solution, taking three aliquot of the colloidal gold solution and adjusting pH to 7.5-8.5, respectively, Adding the three antibodies of the markers into the three aliquot of the colloidal gold solution in the way that add 0.5-2 mg antibody into 100 ml colloidal gold solution, respectively, stirring 1.5-3 h at room temperature, adding bovine serum albumin and polyethylene glycol to block the surface of the colloidal gold solution, centrifuging, discarding the supernatant, redissolving the precipitate in colloidal gold work-solution which is borate buffer in pH7.9-8.1 containing 0.8 wt %-1.2 wt % bovine serum albumin, 8 wt %-12 wt % goat serum, 1.5 wt %-2.5 wt % sucrose and 0.1 wt %-0.5 wt % surfactant, then spreading on a glass fiber membrane or non-woven fabrics, drying for 2-5 h in a drying room which has temperature of 20-25° C. and humidity less than 30% to obtain the colloidal gold pad;
(2) preparing the chromatographic membrane, which comprises preparing 0.5-2 mg/ml solutions of the three paired antibodies of the three biomakers with buffer in pH7-8, respectively, preparing 0.5-2 mg/ml solution of goat anti mouse IgG monoclonal or polyclonal antibody with buffer in pH7-8, drawing lines with the four solutions by a dispenser with a parameter of 1-1.5 ul/cm on an upper part, an middle part and a lower part of a nitrocellulose membrane, respectively, to obtain three test lines and one control line, drying for 2-5 h in a drying room which has temperature of 20-25° C. and humidity less than 30%;
(3) assembling the strip, which comprises adhering the sample pad, the conjugate pad, the chromatographic membrane, and a sample absorption pad successively to a plastic base pad in a drying room which has temperature of 20-25° C. and humidity less than 40%, cutting into the strip.

Preferably, in the step (1), adjusting pH of the colloidal gold solution to 8.1-8.3, specifically 8.2 e.g.

Preferably, in the step (1), adding 0.8-1.2 mg MPO antibody into per 100 ml colloidal gold solution, adding 1.3-1.7 mg H-FABP antibody into per 100 ml colloidal gold solution, and adding 0.8-1.2 mg cTnI antibody into per 100 ml colloidal gold solution.

Preferably, in the step (1), the concentration of borate in the colloidal gold solution work solution is 18-22 mM, specifically 20 mM e.g.

Preferably, in the step (2), preparing 1.2-1.8 mg/ml solution with MPO antibody B and H-FABP antibody B, specifically 1.5 mg/ml e.g., and repairing 0.8-1.2 mg/ml solution with cTnI antibody B, specifically 1.0 mg/ml e.g.

Another technical solution of the present invention is as below.

A preparation method of the kit for testing myocardial infarction rapidly comprising following steps:
(1) preparing the colloidal gold pad comprising, which comprises colloidal gold solution, taking three aliquot of the colloidal gold solution and adjusting pH to 7.5-8.5, respectively, Adding the three antibodies of the markers into the three aliquot of the colloidal gold solution in the way that add 0.5-2 mg antibody into per 100 ml colloidal gold solution, respectively, stirring 1.5-3 h at room temperature, adding bovine serum albumin and polyethylene glycol to block the surface of the colloidal gold solution, centrifuging, discarding the supernatant, redissolving the precipitate in colloidal gold work-solution to obtain solution A, diluting biotin-labeled cTnI paired antibody with PBS buffer to 0.5-2 mg/ml to obtain solution B, then spreading solutions A and B on a glass fiber membrane or non-woven fabrics, drying for 2-5 h in a drying room which has temperature of 20-25° C. and humidity less than 30% to obtain the colloidal gold pad;
(2) preparing the chromatographic membrane, which comprises preparing 0.5-2 mg/ml solutions of the three paired antibodies of the three biomakers with buffer in pH7-8, respectively, preparing 0.5-2 mg/ml solution of streptavidin, preparing 0.5-2 mg/ml solution of goat anti mouse IgG monoclonal or polyclonal antibody with buffer in pH7-8, drawing lines with the four solutions by a dispenser with a parameter of 1-1.5 ul/cm on an upper part, an middle part and a lower part of a nitrocellulose membrane, respectively, to obtain three test lines and one control line, drying for 2-5 h in a drying room which has temperature of 20-25° C. and humidity less than 30%;
(2) preparation the chromatographic membrane, which comprises preparing 0.5-2 mg/ml solutions of the paired antibodies of the three makers with buffer in pH7-8, respectively, preparing 0.5-2 mg/ml solution of goat anti mouse IgG monoclonal or polyclonal antibody with buffer in pH7-8, drawing lines with the four solutions by a dispenser with a parameter of 1-1.5 ul/cm on an upper part, an middle part and a lower part of a nitrocellulose membrane, respectively, to obtain three test lines and one quality control line, drying for 2-5 h in a drying room which has temperature of 20-25° C. and humidity less than 30%;
(3) assembling the strip, which comprises adhering the sample pad, the conjugate pad, the chromatographic membrane, and a sample absorption pad successively to a plastic base pad in a drying room which has temperature of 20-25° C. and humidity less than 40%, cutting into the strip.

Preferably, in the step (1), adjusting pH of the colloidal gold solution to 8.1-8.3, specifically 8.2 e.g.

Preferably, in the step (1), adding 0.8-1.2 mg MPO antibody into per 100 ml colloidal gold solution, adding 1.3-1.7 mg H-FABP antibody into per 100 ml colloidal gold solution, and adding 0.8-1.2 mg cTnI antibody into per 100 ml colloidal gold solution.

Preferably, in the step (1), the concentration of borate in the colloidal gold solution work solution is 18-22 mM, specifically 20 mM e.g.

Preferably, in the step (2), preparing 1.2-1.8 mg/ml solution with MPO antibody B and H-FABP antibody B, specifically 1.5 mg/ml e.g., and preparing 0.8-1.2 mg/ml solution with cTnI antibody B, specifically 1.0 mg/ml e.g.

The present invention also simultaneously provides a preparation method of the kit for testing myocardial infarction rapidly comprising following steps:
(1) preparing the fluorescence microparticles conjugate pad comprising mixing the fluorescence microparticles with the three markers antibodies to obtain the antibody labeled fluorescence microparticles, then spreading the antibody labeled fluorescence microparticles on a glass fiber membrane or non-woven fabrics to obtain the fluorescence microparticles conjugate pad;
(2) preparing the chromatographic membrane, which comprises preparing 0.5-2 mg/ml solutions of the three paired antibodies of the three markers with buffer in pH7-8, respectively, preparing 0.5-2 mg/ml solution of goat anti mouse IgG monoclonal or polyclonal antibody with buffer in pH7-

8, drawing lines with the four solutions by a dispenser with a parameter of 1-1.5 ul/cm on an upper part, an middle part and a lower part of a nitrocellulose membrane, respectively, to obtain three test lines and one control line, drying for 2-5 h in a drying room which has temperature of 20-25° C. and humidity less than 30%;

(3) assembling the strip, which comprises adhering the sample pad, the conjugate pad, the chromatographic membrane, and a sample absorption pad successively to a plastic base pad in a drying room which has temperature of 20-25° C. and humidity less than 40%, cutting into the strip.

Furthermore, the fluorescent substance is an excited fluorescent substance.

According to the present invention, the chromatographic membrane is preferably a nitrocellulose membrane. The control line on the chromatographic membrane is preferably formed by coating with goat anti-mouse IgG monoclonal or polyclonal antibody.

Preferably, enclose the test strip into a plastic card to form a test paper card.

Preferably, all the antibodies and paired antibodies of the three markers are hypersensitive specific antibodies, which are company's own products or purchased products.

Another technical solution of the present invention is as below.

Use of the kit for testing myocardial infarction rapidly for early warning and monitoring of myocardial infarction.

Due to the use of the above technical solutions, the present invention has the following advantages and effects over the prior art:

The kit combines the three specific markers of myocardial infarction on one strip to detect, and has advantages such as convenient operation, rapid response, high sensitivity and high specificity, point of care test, and economical and practical etc. The kit provides early warning, classifying and clinical diagnosing of myocardial infarction for patients with Chest Pain. The kit overcomes the deficiencies of the prior art, to achieve maximum economic and social benefit.

DETAILED DESCRIPTION OF EXEMPLARY EMBODIMENTS

Myocardial infarction is a life-threatening and acute disease, which is time-limited in diagnosing and rescuing. The significance of quickly and convenient diagnosing myocardial infarction is greater than any other disease. Since traditional individual biomarker has lower sensitivity and accuracy, it can't be decide if there is myocardial infarction or other disease (such as some inflammation can cause MPO increased) by doctor or patient in the absence of other detect equipment such as electrocardiograph, cardiac ultrasound.

Detected by the kit of this invention, Myocardial infarction can be confirmed if two markers show positive result. It avoided one-sidedness and inaccuracy of existing individual biomarker kit. A clinical study enrolled 16 negative and 16 positive samples by cTnI kit detecting, showed that the kit of this invention can be more comprehensive and accurate for myocardial infarction patients to make early diagnosis.

Furthermore, the present invention kit provides a point of care test, patients can do self-test at home or anywhere, to avoid experience adverse heart events due to misdiagnosis (the symptoms of early myocardial infarction are similar with that of stomach or frozen, and easily to be ignored to cause serious consequences, even death). The product of this invention changes this situation completely, the patients having the risk of MI such as a family history, hyperglycemia, hypertension and hyperglycemia, diabetes, etc. can prepare the kit in hand. If any uncomfortable symptoms appears (such as stomach pain, shoulder pain, arm numbness, dizziness, even nausea, vomiting, sweating, bradycardia, dyspnea, etc.), he/she can test by himself or his/her family. When a positive line is shown, it is recommended to rush to the hospital emergency room; if more than two test lines are positive, indicate that there is more than 95% possibility of MI, called an emergency ambulance immediately. If 3 positive test lines are shown, tell the doctor that it is MI and need treatment immediately. In addition, it takes short time to do a test; the result can be read in 5-15 minutes to avoid adverse events.

Compared with the conventional method of the preparation of similar products, the present invention as a multiple indicator combination product needs a more specific marker, finer targeting, and its technology and formulation screening are more complex. The production process is very complicated, such as screening and purification of specific antibodies, selection concentration of the marker antibody, crossover control reaction conditions. It needs for repeated detecting and verification. The present invention will be described in detail combined with specific embodiments in below, but the present invention is not limited to the following embodiments.

Embodiment 1 preparation methods and detection methods of human myeloperoxidase-heart-fatty acid binding protein-cardiac troponin I triple colloidal gold rapid quantitative detection kit (hereinafter referred as MPO-FABP3-cTnI triple colloidal gold kit).

Example 1: Preparation of MPO-FABP3-cTnI Triple Colloidal Gold Kit

1. Main Material

Standard substances of MPO, FABP3 and cTnI: National Institute for the Control of Pharmaceutical and Biological Products.

Antibodies and specific paired antibodies of MPO, FABP3: Shanghai Enzyme-linked Biotechnology Co., Ltd.

Antibodies and specific paired antibodies of cTnI: Shanghai Linc-Bio Science Co., Ltd.

Streptavidin: Thermo.

Antibody of goat anti-mouse IgG: Hangzhou Kitgen Bio-tech Co., Ltd.

Chloroauric acid: Sigma.

Nitrocellulose (NC) membrane: SARTORIUS (Germany), CN140.

Bovine serum albumin (BSA), polyethylene glycol PEG20000, casein hydrolyzate: Sigma.

Other reagents are analytical grade reagents.

Clinical samples: 200 quantified serum samples from the relevant hospital, the content distribution intervals of MPO, FABP3 and cTnI content are 6.25-400 ng/ml, 3.125-200 ng/ml, and 0.1-25 ng/ml, respectively.

2. MPO-FABP3-cTnI Triple Colloidal Gold Kit Preparation Method Comprises Following Steps:

(1) Colloidal Gold-Labeled MPO Antibody, FABP3 Antibody and cTnI Antibody

Prepared 15 nm-50 nm colloidal gold solution with sodium citrate reduction method, taked three aliquot of the colloidal gold solution, adjusted the solution to pH7.5, pH8.0 and pH8.5 with 0.2M $K_2CO_3$, respectively. Stirred the solution slowly on a magnetic stirrer, added MPO, FABP3, cTnI antibody using for labeled into colloidal gold solution in the way that add 0.5 mg, 1 mg, 1.5 mg into per 100 ml solution slowly, and stirred for 2 hours continually, then added PEG20000 having a final concentration of 1% and BSA having a final concentration of 1% to block 20 min, 12000 r/m centrifuged after complete marking, discard the supernatant, redissolved the precipitate at 50% of the original volume in colloidal gold work-solution (20 mM borate buffer, pH8.0, which contains 1% BSA, 10% goat serum, 2% sucrose and 0.2% Tween-20). According to the proportion of spread 1 ml solution to 20 cm$^2$, spread the labeled colloidal gold solution on a glass fiber membrane or non-woven fabric, dried for 2-5 h in a drying room which has temperature of 20-25° C. and humidity less than 30% to obtain the colloidal gold pad.

(2) NC Membrane Coating

The MPO paired antibodies, FABP3 paired antibodies and cTnI paired antibodies were diluted to 0.5 mg/ml, 1 mg/ml, 1.5 mg/ml, respectively, with 0.01M pH7.4 PBS. The goat anti-mouse IgG was diluted to 1 mg/ml, 2 mg/ml. Then draw lines by a dispenser with 1.2 ul/cm on a NC membrane to coat, respectively. The NC membrane was dried for 2-5 h in a drying room which has temperature of 20-25° C. and humidity less than 30%. Three test lines and one control line are parallel and are sequentially arranged along the length of the chromatographic membrane.

(3) Strip Assembly

In the drying room which has temperature of 20-25° C. and humidity less than 40%, the coated NC film was placed in the middle of the plastic base pade, colloidal gold pad was cut into appropriate width, the T (test) line side NC membrane touched the colloidal gold conjugate pad and ¼ of NC membrane touching the colloidal gold conjugate pad was pasted. The other side of the colloidal gold conjugate pad touched the sample pad and ⅓ of the colloidal gold conjugate pad touching the colloidal gold conjugate pad was pasted. The C (quality control) side of the NC membrane touched the absorbent pad and ¹⁄₁₀ of the NC membrane touching the absorbent pad paste. Finally cut the plastic pad into 3-5 mm wide test strips with cutting machine, and then put a test strip into a plastic card to form strip card. In the strip, the test line close to the conjugate pad formed by MPO paired antibody, the test line close to the absorbent pad formed by cTnI paired antibody, and the test line in the middle is formed by the FABP3 paired antibody.

(4) Preparation of Colourimetric Card and Instrument Curve Parameters Setting

The following standard samples were test by the strips, respectively, 400, 200, 100, 50, 25, 12.5, 6.25 ng/ml of MPO standard samples, 200, 100, 50, 25, 12.5, 6.25, 3.125 ng/ml of FABP3 standard samples and 20.0, 10.0, 5.0, 2.0, 0.5, 0.1 ng/ml cTnI standard samples. The color band of the test line showed a different intensity with different concentrations of the standard sample printed the color band of corresponding intensity on the colorimetric card to finish the preparation of the colourimetric card. Digitized the color band of corresponding strength band and inputted into the colloidal gold quantitative reader to complete instrument curve parameters setting.

Example 2: Preparation of MPO-FABP3-cTnI Triple Colloidal Gold Kit

1. Main Material

Standard substances of MPO, FABP3 and cTnI: National Institute for the Control of Pharmaceutical and Biological Products.

Antibodies and specific paired antibodies of MPO, FABP3: Shanghai Enzyme-linked Biotechnology Co., Ltd.

Antibodies and specific paired antibodies of cTnI: Shanghai Linc-Bio Science Co., Ltd.

Streptavidin: Thermo.

Antibody of goat anti-mouse IgG: Hangzhou Kitgen Bio-tech Co., Ltd.

Chloroauric acid: Sigma.

Nitrocellulose (NC) membrane: SARTORIUS (Germany), CN140.

Bovine serum albumin (BSA), polyethylene glycol PEG20000, casein hydrolyzate: Sigma.

Other reagents are analytical grade reagents.

Clinical samples: 200 quantified serum samples from the relevant hospital, the content distribution intervals of MPO, FABP3 and cTnI content are 6.25-400 ng/ml, 3.125-200 ng/ml, and 0.1-25 ng/ml, respectively.

2. MPO-FABP3-cTnI Triple Colloidal Gold Kit Preparation Method Comprises the Following Steps:

(1) Colloidal Gold-Labeled MPO Antibody, FABP3 Antibody and cTnI Antibody

Prepared 15 nm-50 nm colloidal gold solution with sodium citrate reduction method, take three aliquot of the colloidal gold solution, adjusted the solution to pH7.5, pH8.0 and pH8.5 with 0.2M $K_2CO_3$, respectively. Stirred the solution slowly on a magnetic stirrer, added MPO, FABP3, cTnI antibody using for labeled into colloidal gold solution in the way that add 0.5 mg, 1 mg, 1.5 mg into per 100 ml solution slowly, and stirred for 2 hours continually, then added PEG20000 having a final concentration of 1% and BSA having a final concentration of 1% to block 20 min, 12000 r/m centrifuged after complete marking, discard the supernatant, redissolved the precipitate at 50% of the original volume in colloidal gold work-solution (20 mM borate buffer, pH8.0, which contains 1% BSA, 10% goat serum, 2% sucrose and 0.2% Tween-20). According to the proportion of spread 1 ml solution to 20 cm$^2$, spread the labeled colloidal gold solution on a glass fiber membrane or non-woven fabric, dried for 2-5 h in a drying room which has temperature of 20-25° C. and humidity less than 30% to obtain the colloidal gold pad.

(2) NC Membrane Coating

The MPO paired antibodies, FABP3 paired antibodies and cTnI paired antibodies were diluted to 0.5 mg/ml, 1 mg/ml, 1.5 mg/ml, respectively, with 0.01M pH7.4 PBS. The goat anti-mouse IgG was diluted to 1 mg/ml, 2 mg/ml with 0.01M pH7.4 PBS, respectively. Then draw lines by a dispenser with 1.2 ul/cm on a NC membrane to coat, respectively. The NC membrane was dried for 2-5 h in a drying room which has temperature of 20-25° C. and humidity less than 30%. Three test lines and one control line are parallel and are sequentially arranged along the length of the chromatographic membrane.

(3) Assembling the Strip

In the drying room which has temperature of 20-25° C. and humidity less than 40%, the coated NC film was placed in the middle of the plastic base pad, colloidal gold pad was cut into fit width, the T line side NC membrane touched the colloidal gold conjugate pad and ¼ of NC membrane touching the colloidal gold conjugate pad was pasted. The other side of the colloidal gold conjugate pad touched the sample pad and ⅓ of the colloidal gold conjugate pad touching the colloidal gold conjugate pad was pasted. The C line side of the NC membrane touched the absorbent pad and ¹⁄₁₀ of the NC membrane touching the absorbent pad paste. Finally cut the plastic pad into 3-5 mm wide test strips with cutting machine, and then put a test strip into a plastic card to form test paper card. In the strip, the test line close to the conjugate pad formed by MPO paired antibody, the test line close to the absorbent pad formed by cTnI paired antibody, the test line in the middle is formed by the FABP3 paired antibody.

(4) Preparation of Colourimetric Card and Instrument Curve Parameters Setting

The following standard samples were test by the strips, respectively, 400, 200, 100, 50, 25, 12.5, 6.25 ng/ml of MPO standard samples, 200, 100, 50, 25, 12.5, 6.25, 3.125 ng/ml of FABP3 standard samples and 30, 20, 10, 5, 1, 0.5, 0.1 ng/ml cTnI standard samples. The color band of the test line showed a different intensity with different concentrations of the standard sample printed the color band of corresponding intensity on the colorimetric card to finish the preparation of the colourimetric card. Digitized the color band of corresponding strength band and inputted into the colloidal gold quantitative reader to complete instrument curve parameters setting.

Example 3: Detection Method of MPO-FABP3-cTnI Colloidal Gold Triple Kit (1) Equilibrate the temperature of the detection reagents and samples to room temperature, remove the paper cards and flat;

(2) Draw 10 μl serum and plasma samples precisely, the samples is draw 20 ul when whole blood, add into clean centrifuge tube, dilute 10 times with sample dilution (PBS) and mix well;

(3) Draw 50-100 μl sample which is diluted with pipette and added into sample well, using colloidal gold quantitative reader or quantitative colorimetric card reader (half) to determination determine result quantitatively within 15 to 20 minutes.

When determine by instrument, set the instrumental parameters and put the test paper card into the warehouse to detect. The instrument will show the results of the quantitative determination of the concentration of the sample.

When use the colorimetric card to determine the results, compare the shades of color of the T-line to the color of the standard line to semi-quantitative determine the concentration of the sample interval. Use the test strip produced by method of Example 1, to test 100 clinical samples, determine by colloidal gold detector, average deviations of 95 samples in the detection range are less than 15%, the maximum deviation is less than 20%, $R^2>0.97$, consistency coefficient>0.88. When the result of the determination by colorimetric card, the coincidence rate of the result of interval determines determination and the value of samples is 95.5%, consistency coefficient>0.85.

Criteria of the present invention test results: When the test line appears two positive bands, can be diagnosed as myocardial infarction.

Test results showed the detection kit preparation has good performance and is suitable for clinical detecting and meets different needs of different customers in different detection occasions.

Example 4. Clinical Sample Results-1

Detected patients who have been clinical diagnosed with myocardial infarction by the test strip produced by method of Example 1. Random chose serum samples of 16 patients with myocardial infarction were detected to verify. The detected value of MPO and FABP3 were above Medicine decided level. That shows patients with MI, MI prediction accuracy rate reached 100%, the accuracy of troponin detected myocardial infarction was 50%. This shows present invention can be significantly better than the old index detector in the accuracy of diagnosis and early warning of myocardial infarction. Test results are shown in Table 1.

TABLE 1

The serum results of MPO-FABP3-cTnI triple colloidal gold kit for the detection of patients with myocardial infarction

| Serial number | age | cTnI (ng/ml) | MPO (ng/ml) | FABP3 (ng/ml) |
|---|---|---|---|---|
| 1 | 81 | 0.1 | 4173.51 | 108.21 |
| 2 | 69 | 0.1 | 613.57 | 85.46 |
| 3 | 85 | 0.1 | 730.76 | 82.04 |
| 4 | 66 | 0.1 | 982.57 | 60.20 |
| 5 | 84 | 0.2 | 3020.53 | 115.98 |
| 6 | 71 | 0.3 | 843.48 | 55.72 |
| 7 | 76 | 0.3 | 1127.26 | 142.40 |
| 8 | 74 | 0.6 | 669.95 | 47.35 |
| 9 | 80 | 0.7 | 1387.99 | 86.25 |
| 10 | 76 | 0.8 | 1607.77 | 67.34 |
| 11 | 64 | 1.7 | 1809 | 78.18 |
| 12 | 70 | 1.8 | 1990 | 53.95 |
| 13 | 67 | 1.8 | 1973.09 | 75.3 |
| 14 | 3 | 2.3 | 2585.02 | 120.78 |
| 15 | 69 | 4.6 | 4195.51 | 91.44 |
| 16 | 60 | 24.3 | 675.08 | 98.55 |

Example 5. Clinical Sample Results-2

Use by the test strips produced by the method of Example 2, determined by colloidal gold detection instrument, the average deviation was less than 15%, the maximum deviation was less than 20%, $R^2>0.98$. When the result was determined by standard colorimetric card, the coincidence rate of the result of interval determines determination and the value of samples was 95%, and the consistency coefficient was more than 0.95.

32 MI samples, with Myoglobin clinical test negative and medical imaging diagnosis positive, were test by the triple kit. The result of MPO and FABP3 were all above the medicine decide level that shows patients with MI, MI prediction accuracy rate reached 100%. The cTnI test only showed 23 were above threshold, that shows patients with MI, MI prediction accuracy rate reached 71.8%. Further shows that the diagnose accuracy of cTnI is pending. The results indicated that accuracy of this present invention is much better than the conventional models. Test results are shown in Table 2.

TABLE 2

The serum results of MPO-FABP3-cTnI colloidal gold triple kit for the detection of patients with negative results

| Serial number | age | cTnI (ng/ml) | MPO (ng/ml) | FABP3 (ng/ml) |
|---|---|---|---|---|
| 1 | 64 | 2 | 500 | 171.41 |
| 2 | 83 | 9.5 | 1252 | 15.32 |
| 3 | 66 | 0.1 | 982 | 60.20 |
| 4 | 85 | 0.1 | 730 | 82.04 |
| 5 | 40 | 1.3 | 1014 | 10.07 |
| 6 | 82 | 3.3 | 1051 | 95.69 |
| 7 | 90 | 5.6 | 1921 | 26.61 |
| 8 | 67 | <0.1 | 471 | 185.00 |
| 9 | 78 | <0.1 | 760 | 161.63 |
| 10 | 3 | 2.3 | 2585 | 120.78 |
| 11 | 69 | 6 | 2184 | 46.14 |
| 12 | 74 | 0.6 | 669 | 47.35 |
| 13 | 47 | 0.7 | 441 | 14.79 |
| 14 | 82 | 0.7 | 770 | 186.77 |

TABLE 2-continued

The serum results of MPO-FABP3-cTnI colloidal gold triple kit for the detection of patients with negative results

| Serial number | age | cTnI (ng/ml) | MPO (ng/ml) | FABP3 (ng/ml) |
|---|---|---|---|---|
| 15 | 70 | 2.2 | 1213 | 24.14 |
| 16 | 80 | 3.5 | 853 | 39.22 |
| 17 | 69 | 7.3 | 6792 | 36.65 |
| 18 | 80 | 0.7 | 1387 | 86.25 |
| 19 | 70 | 1.8 | 1990 | 53.95 |
| 20 | 47 | 6.3 | 827 | 19.84 |
| 21 | 60 | 24.3 | 675 | 98.55 |
| 22 | 88 | 12.1 | 626 | 17.07 |
| 23 | 83 | <0.1 | 714 | 69.81 |
| 24 | 84 | <0.1 | 1385 | 193.55 |
| 25 | 67 | 1.4 | 1680 | 52.10 |
| 26 | 82 | 1.5 | 787 | 20.06 |
| 27 | 67 | 0.5 | 1503 | 18.84 |
| 28 | 82 | 5.4 | 1038 | 14.52 |
| 29 | 76 | 0.3 | 1127 | 142.40 |
| 30 | 79 | 2.6 | 1062 | 229.77 |
| 31 | 47 | <0.1 | 1990 | 69.51 |
| 32 | 69 | 0.1 | 613 | 85.46 |

Embodiment 2 Preparation and Detection Methods of the MPO-FABP3-cTnI Triple Immunofluorescence Kit (Hereinafter Referred as MPO-FABP3-cTnI Triple Immunofluorescence Kit)

Example 1 Preparation of MPO-FABP3-cTnI Triple Immunofluorescence Kit

1. Main Material

Standard substances of MPO, FABP3 and cTnI: National Institute for the Control of Pharmaceutical and Biological Products.

Antibodies and specific paired antibodies of MPO, FABP3: Shanghai Enzyme-linked Biotechnology Co., Ltd.

Antibodies and specific paired antibodies of cTnI: Shanghai Linc-Bio Science Co., Ltd.

EU-fluorescent microspheres: Model RM100-010-EU, the micrometer Shanghai biological products Nitrocellulose (NC) membrane: SARTORIUS (Germany), CN140.

Bovine serum albumin (BSA), polyethylene glycol PEG20000, casein hydrolyzate: Sigma.

Antibody of goat anti-mouse IgG: Hangzhou Kitgen Bio-tech Co., Ltd. Other reagents are analytical grade reagents.

Clinical samples were obtained from the relevant hospital, a total of 200 copies serum.

2. The Preparation Method Comprises Following Steps:
(1) Immunofluorescence Labeling the MPO Antibody, FABP3 Antibody and cTnI Antibody.

The PB buffer and fluorescent microspheres solution were successively added to the centrifuge tube, then blowing and mixing with pipettor, recorded as microsphere system. The EDC solution prepared with PB buffer was added into the microsphere system, immediately blowing and mixing with pipettor, reaction for 30 minutes within which blowing with pipettor more than once, recorded as activation system. Take MPO antibody, FABP3 antibody and cTnI antibody solution, diluted with PB buffer, recorded as diluted antibody. When the activation time was over, the diluted antibody was added into the activation system, immediately blowing and mixing with pipettor, reaction for 2 hours at room temperature, recorded as reaction system. After the reaction was completed, the reaction system was centrifuged at 14000 rpm for 20 min at 8° C. The supernatant was discarded and the precipitate was re-suspended in 100 μL re-suspension, to get a fluorescent microsphere containing labeled antibody.

(2) Preparing the Fluorescence Microparticles Conjugate Pad.

The labeled fluorescence microparticles solution from step (1) was spread on a glass fiber membrane or non-woven fabrics, dried for 2-5 h in a drying room which has temperature of 20-25° C. and humidity less than 30%.

(3) NC Membrane Coating

The MPO paired antibody, FABP3 paired antibody and cTnI paired antibody were respectively diluted to 1.0 mg/ml, 1.5 mg/ml, 2.0 mg/ml with PBS buffer (0.01M, pH7.4), and goat anti mouse monoclonal or polyclonal antibody was diluted to 0.5 mg/ml and 1.0 mg/ml with PBS buffer (0.01M, pH7.4), respectively. Then draw lines by a dispenser with 1.2 ul/cm on a NC membrane to coat, respectively. The NC membrane was dried for 2-5 h in a drying room which has temperature of 20-25° C. and humidity less than 30%. The dried NC membrane was placed in blocking solution (0.01% pH 7.4 PBS containing 1% BSA, 1% sucrose) at 37° C. for 1 hour, taken out and dried at 37° C. for 2 hours.

(4) Assembling the Strip

It a 20-25° C., less than 40% humidity dry room, the NC membrane was placed in the middle of the plastic pad, the conjugate pad was cut into appropriate width, and then overlapped on the T line side of the NC membrane, the sample pad was overlapped on the other side of the conjugate pad, the C line side of the NC membrane was overlapped on the absorbent pad, and finally the plastic pad will be cut into 3-5 mm wide to form a strip, and then put into the plastic card, forming a test paper card.

Example 2 Detection Method of MPO-FABP3-cTnI Triple Immunofluorescence Kit

Comprising following steps:
(1) Equilibrate the temperature of the test reagents and sample to room temperature, remove the test paper card, flat;
(2) Draw 10 μl serum precisely, add to a clean centrifuge tube, dilute 10 times with sample dilution (PBS or saline), and mix well;
(3) Pipette 50-100 μl of the diluted sample into the sample well; determine the quantitative results by FIA kit reader within 15 minutes.

When determine by instrument, set the instrumental parameters, put the test paper card into the warehouse to detect. The instrument will display the sample concentration of quantitative determination.

Take 20 test strips, 30 μl of standard serum containing 0.5 ng/ml cTnI, 60 ng/ml MPO and 6 ng/ml FABP3 were detected by FIA kit reader. The mean deviation of the samples in the detection range was less than 15%; the maximum deviation was less than 15%, R2>0.98, consistency coefficient>0.90. The results showed that the prepared test kit had good performance and was suitable for clinical detection.

Example 3 Detection of Clinical Samples 36 serum samples of MI patients, with myocardial infarction, were detected. Their serum samples for clinical CKMB test results were negative. The serum samples were test by the invention kit, and the results of MPO and FABP3 were all above the medical decision level, the diagnostic coincidence rate was 100%. The results of Troponin test only 16 cases showed positive, the diagnostic accuracy was 44%. The test results are shown in Table 3.

TABLE 3

MPO-FABP3-cTnI triple fluorescence detection kit for CKMB-negative patient's serum test results

| Serial number | age | cTnI (ng/ml) | MPO (ng/ml) | FABP (ng/ml) |
|---|---|---|---|---|
| 1 | 73 | 0.3 | 725.6 | 5.9 |
| 2 | 69 | 7.3 | 6792.2 | 36.65 |
| 3 | 47 | 0.7 | 441.0 | 14.79 |
| 4 | 61 | <0.1 | 4195.5 | 15.72 |
| 5 | 53 | <0.1 | 1419.7 | 20.81 |
| 6 | 83 | <0.1 | 714.3 | 69.81 |
| 7 | 87 | <0.1 | 969.8 | 23.20 |
| 8 | 87 | <0.1 | 1225 | 36.65 |
| 9 | 74 | 0.6 | 669.95 | 47.35 |
| 10 | 68 | <0.1 | 1134.59 | 24.63 |
| 11 | 70 | <0.1 | 2440.62 | 21.77 |
| 12 | 55 | 0.9 | 3459.21 | 102.86 |
| 13 | 80 | 3.5 | 853.85 | 39.22 |
| 14 | 85 | <0.1 | 3410.99 | 42.42 |
| 15 | 73 | 0.2 | 1724.27 | 6.56 |
| 16 | 78 | 0.2 | 6789.07 | 31.90 |
| 17 | 82 | 0.7 | 770.64 | 186.77 |
| 18 | 70 | 2.2 | 1213.67 | 24.14 |
| 19 | 69 | 0.1 | 613.57 | 85.46 |
| 20 | 80 | 0.2 | 880 | 5 |
| 21 | 88 | 6.8 | 450.25 | 51.23 |
| 22 | 82 | 1.5 | 787.14 | 20.06 |
| 23 | 88 | 6.8 | 756 | 18.3 |
| 24 | 68 | <0.1 | 2423.43 | 37.29 |
| 25 | 85 | 0.5 | 5363.27 | 36.32 |
| 26 | 73 | 0.1 | 666.4 | 18.44 |
| 27 | 84 | 0.2 | 3020.53 | 115.98 |
| 28 | 84 | <0.1 | 2825.78 | 179.14 |
| 29 | 88 | 12.1 | 626.4 | 17.07 |
| 30 | 73 | 3.4 | 809.39 | 50.75 |
| 31 | 64 | 2 | 500.95 | 171.41 |
| 32 | 83 | 9.5 | 1252.36 | 15.32 |
| 33 | 82 | 5.8 | 1000.83 | 14.75 |
| 34 | 70 | 0.1 | 2878.59 | 37.01 |
| 35 | 84 | <0.1 | 1385.89 | 193.55 |
| 36 | 84 | 0.3 | 3633.45 | 115.13 |

The above embodiments disclosed herein for the technical concept and feature of the present invention intended to enable those skills in the art to be understood and to carry out without departing from the scope of the present invention. Equivalent variations or modifications in accordance with the present invention are intended to be encompassed within the scope of the present invention.

The invention claimed is:

1. A kit for testing myocardial infarction rapidly, comprising a strip capable of detecting three markers, namely, human myeloperoxidase, heart-fatty acid binding protein and cardiac troponin I simultaneously;
   wherein the strip comprises a sample pad, a conjugate pad, a chromatographic membrane coated with three test lines and a quality control line, and a sample absorption pad, antibodies of the three markers being all marked on the conjugate pad, and the chromatographic membrane having three test lines formed by coating paired antibodies of the three markers respectively, the paired antibodies of the three markers being able to specifically combine with the three markers, respectively;
   wherein the antibodies of the three markers are anti-human myeloperoxidase mouse monoclonal antibody, anti-heart-fatty acid binding protein mouse monoclonal antibody and anti-cardiac troponin I mouse monoclonal antibody, respectively, paired antibodies of the three markers are anti-human myeloperoxidase monoclonal or polyclonal antibody, anti-heart-fatty acid binding protein monoclonal or polyclonal antibody, and anti-cardiac troponin I monoclonal or polyclonal antibody, respectively; and
   wherein the sample pad, the conjugate pad, the chromatographic membrane and the absorbent pad are stickered on a base pad successively, the three test lines of the chromatographic membrane are parallel and are sequentially arranged along the length of the chromatographic membrane, the test line close to the conjugate pad coats paired antibody of human myeloperoxidase, the test line close to the absorbent pad coats paired antibody of cardiac troponin I, and the test line in the middle coats paired antibody of heart-fatty acid binding protein.

2. The kit for testing myocardial infarction rapidly according to claim 1, wherein the conjugate pad is a colloidal gold pad and the kit is a colloidal gold immunoassay kit.

3. The kit for testing myocardial infarction rapidly according to claim 2, wherein the kit further comprises a colourimetric card and/or a colloidal gold quantitative reader.

4. The kit for testing myocardial infarction rapidly according to claim 3, wherein the kit comprises a colourimetric card, the colourimetric card comprises three lines from light to dark red which are printed on a white background which are standard lines of the three markers, respectively, the different shades of color of each red line represent different concentrations of each standard sample.

5. The kit for testing myocardial infarction rapidly according to claim 1, wherein the conjugate pad is a fluorescence microparticles conjugate pad, and the kit is a fluorescence microparticles immunoassay kit.

6. The kit for testing myocardial infarction rapidly according to claim 5, wherein the kit further comprises an immunofluorescence quantitative reader.

7. A preparation method of the kit for testing myocardial infarction rapidly according to claim 1, comprising following steps:
   (1) preparing the colloidal gold pad, which comprises preparing colloidal gold solution, taking three aliquot of the colloidal gold solution and adjusting pH to 7.5-8.5, respectively, adding the antibodies of the three markers into the three aliquot of the colloidal gold solution in the way that add 0.5-2 mg antibody into per 100 ml colloidal gold solution, respectively, stirring 1.5-3 h at room temperature, adding bovine serum albumin and polyethylene glycol to block the surface of the colloidal gold solution, centrifuging, discarding the supernatant, redissolving the precipitate in colloidal gold work-solution which is borate buffer in pH7.9-8.1 and contains 0.8 wt %-1.2 wt % bovine serum albumin, 8 wt %-12 wt % goat serum, 1.5 wt %-2.5 wt % sucrose and 0.1 wt %-0.5 wt % surfactant, then spreading on a glass fiber membrane or non-woven fabrics, drying for 2-5 h in a drying room which has temperature of 20-25° C. and humidity less than 30% to obtain the colloidal gold pad;
   (2) preparing the chromatographic membrane, which comprises preparing 0.5-2 mg/ml solutions of the paired antibodies of the three makers with buffer in pH7-8, respectively, preparing 0.5-2 mg/ml solution of goat anti mouse IgG monoclonal or polyclonal antibody with buffer in pH7-8, drawing lines with the four solutions by a dispenser with a parameter of 1-1.5 ul/cm on an upper part, a middle part and a lower part of a nitrocellulose membrane, respectively, to obtain three test lines and one quality control line, drying for 2-5 h in a drying room which has temperature of 20-25° C. and humidity less than 30%;

(3) assembling the strip, which comprises adhering the sample pad, the conjugate pad, the chromatographic membrane, and a sample absorption pad successively to a plastic base pad in a drying room which has temperature of 20-25° C. and humidity less than 40%, cutting into the strip.

8. A preparation method of the kit for testing myocardial infarction rapidly according to claim 1, comprising following steps:

(1) preparing the fluorescence microparticles conjugate pad, which comprises mixing the fluorescence microparticles with the antibodies of the three markers to obtain the antibody labeled fluorescence microparticles, then spreading the antibody labeled fluorescence microparticles on a glass fiber membrane or non-woven fabrics to obtain the fluorescence microparticles conjugate pad;

(2) preparing the chromatographic membrane, which comprises preparing 0.5-2 mg/ml solutions of the paired antibodies of the three makers with buffer in pH7-8, respectively, preparing 0.5-2 mg/ml solution of goat anti mouse IgG monoclonal or polyclonal antibody with buffer in pH7-8, drawing lines with the four solutions by a dispenser with a parameter of 1-1.5 ul/cm on an upper part, a middle part and a lower part of a nitrocellulose membrane, respectively, to obtain three test lines and one quality control line, drying for 2-5 h in a drying room which has temperature of 20-25° C. and humidity less than 30%;

(3) assembling the strip, which comprises adhering the sample pad, the conjugate pad, the chromatographic membrane, and a sample absorption pad successively to a plastic base pad in a drying room which has temperature of 20-25° C. and humidity less than 40%, cutting into the strip.

9. Use of the kit for testing myocardial infarction rapidly according to claim 1 for early warning and monitoring of myocardial infarction.

* * * * *